United States Patent [19]

Schrier

[11] 4,279,479
[45] Jul. 21, 1981

[54] VISION SCREENING KIT

[76] Inventor: Melvin Schrier, 111 Engle St., Tenafly, N.J. 07670

[21] Appl. No.: 154,322

[22] Filed: May 29, 1980

[51] Int. Cl.³ .......................... A61B 3/02; A61B 3/00
[52] U.S. Cl. ........................ 351/37; 351/36; 351/38
[58] Field of Search ................. 351/36, 37, 38, 32, 351/33, 26

[56] References Cited

U.S. PATENT DOCUMENTS

| | | |
|---|---|---|
| 1,500,248 | 7/1924 | Lewis . |
| 1,686,962 | 10/1928 | Deninson . |
| 1,953,268 | 4/1934 | Scott . |
| 1,990,218 | 2/1935 | Bailey . |
| 2,478,662 | 8/1949 | Long .................................. 351/36 X |
| 2,795,993 | 6/1957 | Leverett et al. ....................... 351/36 |

Primary Examiner—John K. Corbin
Assistant Examiner—Rodney Bovernick

[57] ABSTRACT

A simple, inexpensive vision screening device in the form of a compact kit.

7 Claims, 6 Drawing Figures

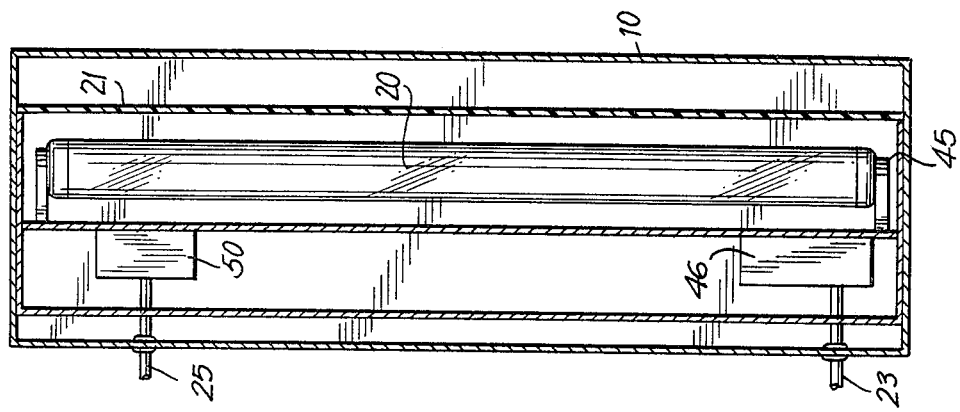
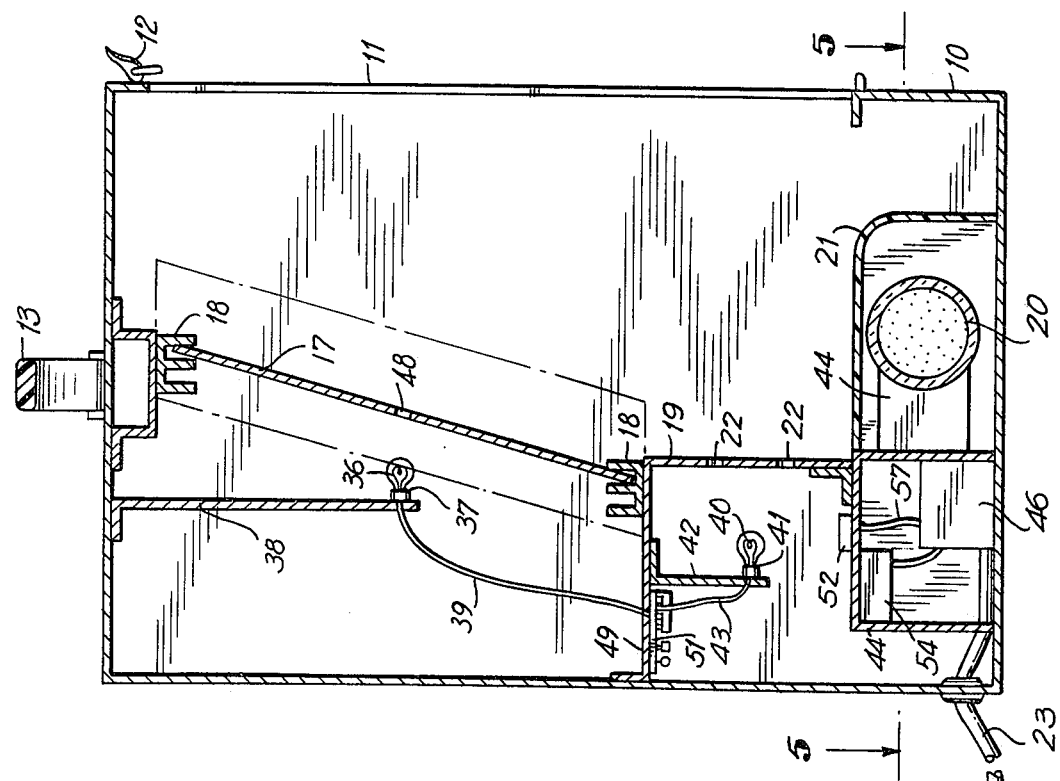
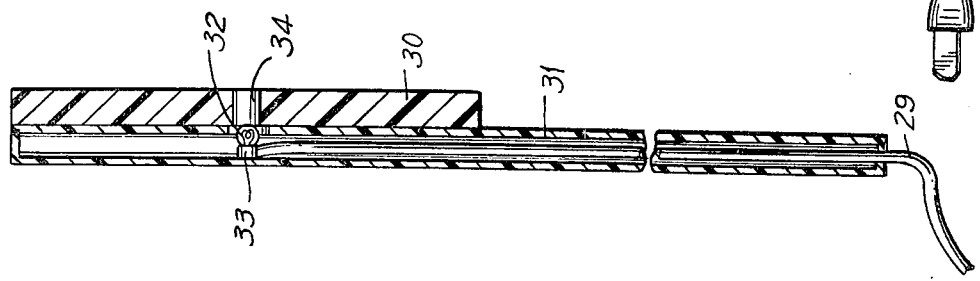

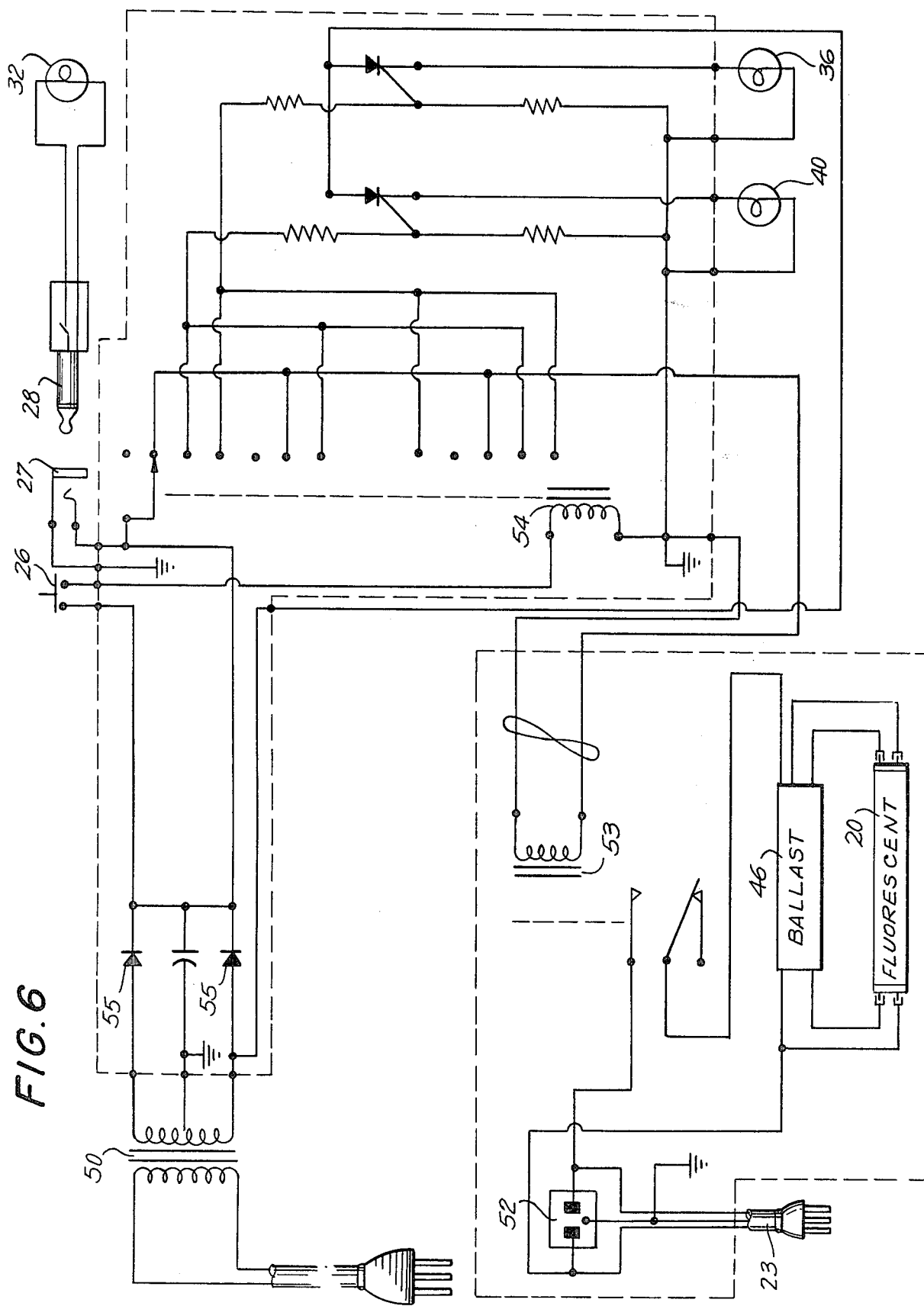

VISION SCREENING KIT

The present invention relates to vision screening equipment and more particularly to improvements in such equipment which permit the equipment to be constructed in the form of an inexpensive, portable, compact kit.

While the prior art discloses that the technique for vision screening is more or less standard procedure, the equipment used for the practice of such procedures has heretofore been rather complex, cumbersome, involved and did not readily lend itself to portability or ease of set-up and use. Typical of the prior art devices are those disclosed in U.S. Pat. No. 2,478,662 to Long and U.S. Pat. No. 3,795,993 to Leverett et al. Both of these devices disclose vision testing kits which require more cumbersome set-ups and involved procedures than are required by the device of the present invention in carrying out the vision screening.

It is an object of the present invention to provide vision screening equipment in the form of a compact portable kit constructed in a manner which permits ready set-up and facilitates simple and rapid vision screening by a non-professional.

Another object of the present invention is to provide a vision screening kit which is a completely self-contained, integral unit requiring only the use of several portable accessories in order to carry out a number of standard vision screening procedures.

Another object of the present invention is to provide a vision screening kit which simplifies the testing procedures and eliminates the need for interpretation of results by non-professional operators.

It is yet another object of the present invention to provide a vision screening kit which may be readily transported and used for mass examinations of student vision by lay persons for purposes of screening to determine whether professional consultation is required.

Other and further objects and advantages of the present invention will be hereinafter described and the novel features thereof defined by the appended claims, taken in connection with the accompanying drawings, in which:

FIG. 3 is a vertical sectional view through a near point vision and phoria screener, as taken on the line 3—3 of FIG. 2;

FIG. 4 is a vertical sectional view through the vision screening equipment taken on the line 4—4 of FIG. 2;

FIG. 5 is a horizontal sectional view through the vision screening equipment taken on the line 5—5 of FIG. 4, showing the details of the electrical component systems contained within the unit;

FIG. 6 is a wiring diagram of the electrical circuits under the conditions provided when the equipment is set up and ready for use.

Figure 1:
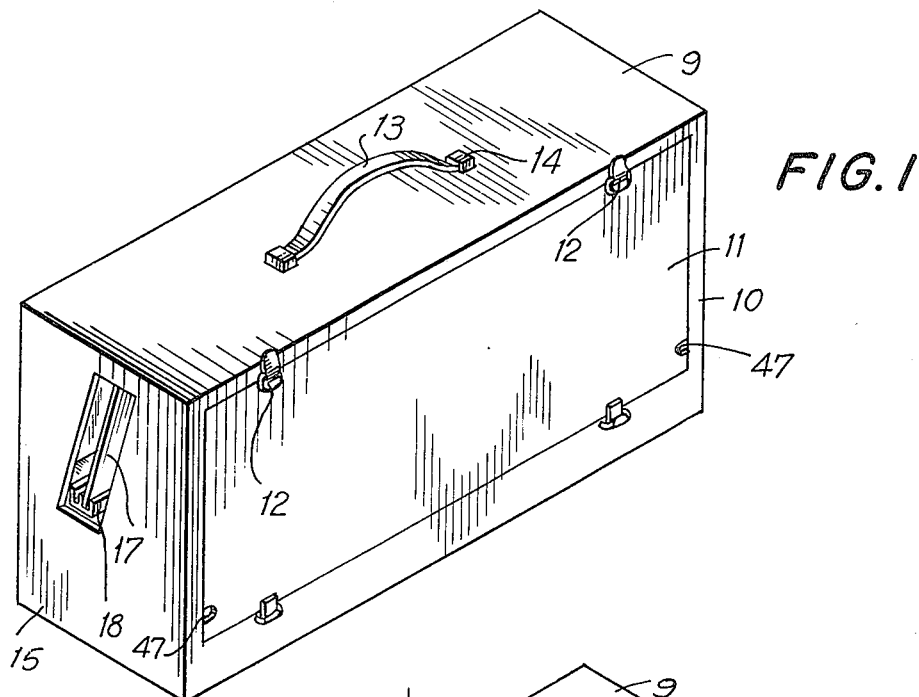
FIG. 1 is a perspective view of the vision screening equipment as housed in a carrying case.
Figure 2:
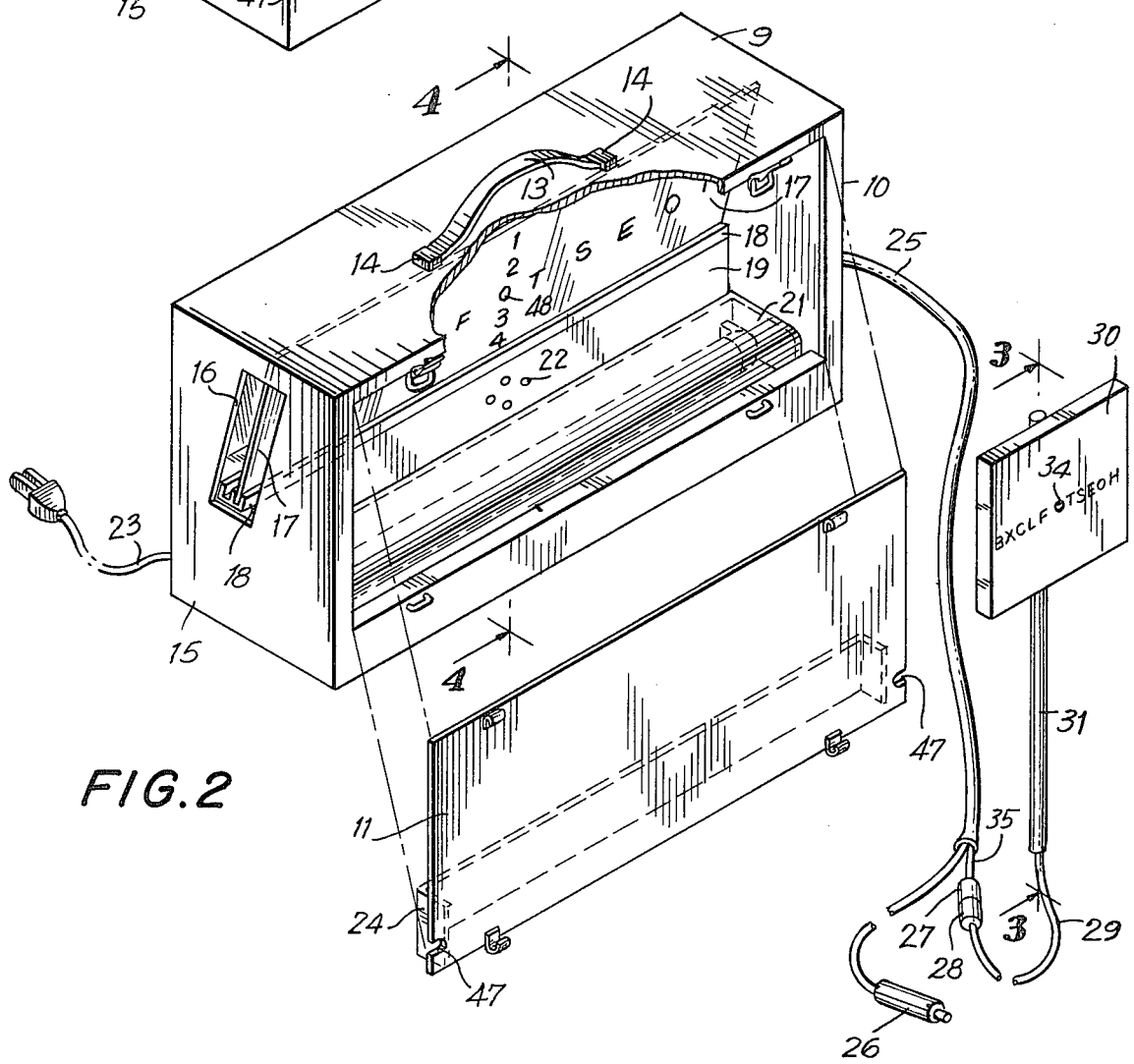
FIG. 2 is a perspective view of the vision screening equipment with the front panel removed, ready to be used for vision screening.

Referring to the drawings wherein like reference characters designate corresponding parts of the several figures of the drawing, numeral 9 denotes the vision screening kit of the present invention having a rectangular shape which may be made of aluminum, other light weight metal, or suitable plastic material whereby the device will be neat, attractive in appearance and durable.

Carrying case 10 has a removable front panel 11 held in place by hasps 12 which are pivotally engaged to lock said panel in position when the equipment is to be carried. Upon opening hasps 12, front panel 11 may be removed, placing the equipment in condition for use. Front panel 11 has a semi-circular cut-out 47,47 in the lower portion of each of its vertical sides of sufficient size to permit power cable 23 and switch cable 25 to pass through. The rear side of front panel 11 has accessory tray 24 mounted thereon to provide storage space for auxiliary equipment used therewith. The top side of carrying case 10 has located thereon a handle 13, fastened either rigidly or pivotally thereto by handle fasteners 14,14. Side panel 15 has a rhomboidal opening 16 of sufficient dimension to permit eye chart 17 to pass through. Eye chart 17 is slidably inserted into opening 16 and held in place by chart track 18,18, the upper and lower portions of said chart track 18,18 each having at least one channel, although two or more channels may be provided if it is desired to store additional charts behind the chart in use. Chart track 18,18 may be constructed of extrudable aluminum, plastic, or other suitable material. Eye chart 17 has a white, opaque coating on its face and has located in the center thereof, lamp opening 48 which is in alignment with lamp 36, preferably a light emitting diode, which provides a small source of illumination.

Electronics housing vertical wall 19 has a Worth 4-Dot Tester located therein which consists of four holes 22 in the center thereof preferably about ½ inch in diameter, two in perpendicular alignment and two in horizontal alignment, and preferably spaced two inches apart from each other with centrally located lamp 40 behind said four holes, although preferably one lamp 40 is located behind each of said holes. Lamp 40 is held in socket 41 which is mounted on bracket 42 to provide a light source, two of said holes having a green film therebehind and one a red film to provide the requisite red and green lights. The fourth hole provides white light. Lamp 20, preferably a fluorescent lamp, held in lamp sockets 45,45 which are mounted on lamp base 44 which is fastened to vertical wall 19 by common fastening means and housed within diffuser 21, provides illumination for chart 17 which also has located in the center thereof lamp opening 48. Located in alignment with lamp opening 48 and mounted therebehind is lamp 36 which is held in socket 37 mounted on bracket 38 which is fastened to electronics housing top 50.

Lamps 20, 36 and 40 are controlled by switch 26 which is connected to said lamps by cable 25 which has a ten foot marking thereon, to permit measuring such distance from vision screener 9 when cable 25 is stretched. Cable 25 also has connected thereto extension 35, near point vision screener coupler 27,28 which preferably is a jack device wherein coupler half 27 is the female and coupler half 28 is the male. Coupler half 28 is connected by cable 29 through hardle 31 to near point vision and near phoria screener chart 30. Cable 29 passes through handle 31 to lamp 33, preferably a light emitting diode, to permit energizing of lamp 32 when current passes therethrough. Centrally located in the near point vision and near phoria screener chart 30 is opening 34. Lamp 32 is located behind opening 34 and is in alignment therewith and held in place by lamp socket 33.

To screen a patient, the patient to be tested is positioned, either sitting or standing, ten feet from vision screener 9 using the distance markings on cable 25 or a conventional measuring tape. Although the use of the present invention has been described with reference to screening at a ten foot distance, it is to be understood that other distances may be employed provided proportionate size scalings are made. When using vision screener 9 at the ten foot distance, removable eye chart 17 preferably has eight letters based on the conventional Snellen configuration, 6.5 millimeters in height, spaced two prism diopters apart in a horizontal line across the face of said chart, with four letters equally spaced on each side of lamp opening 48 and four numbers 6.5 millimeters in height, spaced one prism diopter apart perpendicular to said letters along a line passing perpendicularly through lamp opening 28, with two numbers above and two numbers below said opening. The use of chart 17 enables screening for distance visual acuity when each eye is occluded separately with a standard black occluder which is a screening accessory. When the patient is provided with a pair of +2.00 diopter lens in a frame, which are a screening accessory, distance visual acuity through plus lens can be screened. The patient, if normally wearing glasses, holds the +2.00 diopter lens over the glasses.

Distance lateral phoria is screened by using lamp 36 and a Maddox rod provided as a screening accessory. Distance vertical phoria is screened by shifting the Maddox rod 90° in front of each eye. Near point lateral phoria is screened by use of the light source produced by lamp 32 in hand held near point vision and phoria screener 30 and a Maddox rod. In use the patient holds the near point vision and phoria screener 30 in one hand and the Maddox rod in the other. If the light source produced by lamp 32 is white, a red Maddox rod is used and if the light source is red, a white Maddox rod is used.

Near point visual acuity is screened by having the patient hold near point vision and phoria screener 30 between 12-16 inches from the eyes and reading the ten letters spaced two prism diopters apart, with five letters on each side of lamp opening 34. Preferably the letters are of 20/30 near point in size on the face of screener 30 which may be illuminated with a conventional 75-watt bulb in a gooseneck lamp or other readily available moderate light source.

Binocularity is screened with the Worth 4-Dot Tester 22 located in electronics housing vertical wall 19 using as an accessory, conventional red-green glasses.

In using the device, vision screener 9 is placed on a flat table or hung on a wall. Removable front panel 11 is removed from carrying case 10 by releasing hasps 12. The free end of power cord 23 is removed from carrying case 10 and plugged into a grounded electrical outlet. The free end of switch cable 25 is removed from carrying case 10 and extended to the ten foot marking. The screening accessories are removed from accessory tray 24 and placed on a table or stand next to the patient to be screened. Near point vision and phoria screener 30 is removed from carrying case 10 and coupler half 27 is connected to coupler half 28. Near point vision and phoria screener 30 is placed on the table or stand which is in close proximity to the patient being screened. Lamp 20 is illuminated by switch 26.

With the patient seated and the removable eye chart 17 positioned within vision screener 9, distance visual acuity with normal vision (with or without glasses) is screened by having the patient read the letters or removable eye chart 17, first with the right eye and then with the left eye, in each case the eye not being tested covered with a standard eye occluder.

The patient is then screened for excessive hyperopia by placing a pair of +2.00 diopter lenses over the eyes (with or without glasses) and having the patient read the letters on the removable eye chart 17 with both eyes. If the patient can read the letters he is using excess energy to focus and is referred for professional consultation.

Distance lateral phoria is screened using lamp 36 which acts as a small source of light seen in the center of removable eye chart 17. Switch 26 is operated to illuminate lamp 36. A Maddox rod, one of the testing accessories, is placed before the right eye. The lines in the Maddox rod are lined up horizontally in front of the patient's right eye as he looks at lamp 36. When viewing lamp 36 (white color) through a red Maddox rod, the right eye will see a vertical red line while the left eye will see the small light source produced by lamp 36. If the red line is seen passing through the small light source produced by lamp 36, the eyes are parallel. If the line is seen to the right of the small light source, the patient is esophoric and if the line is seen to the left of the small light source, the patient is exophoric. If the red line is seen at the fourth letter to the left of lamp opening 34 or beyond or at the second letter or beyond to the right of lamp opening 34, the patient is referred.

Distance vertical phoria is screened by having the patient turn the Maddox rod 90° so that the parallel lines are in the vertical position. If the red horizontal line is seen above or below the first numeral which is adjacent to the small light source produced by lamp 36, the patient is referred.

Near point visual acuity is screened by having the patient hold near point vision and phoria screener 30 approximately 12-16 inches from his eyes. Near point vision and phoria screener 30 is illuminated by a conventional 75-watt lamp. First the right eye is covered and then the left eye with a standard eye occluder. If the patient cannot read eight of the ten 20/30 near point letters on the face of near point vision and phoria screener 30 or if the patient assumes an unusual posture as evidenced by tilting of head or holding tester closed than eight inches from eye or squints which indicate possible discomfort, the patient is referred for professional evaluation.

Near point lateral phoria is screened in the same manner as distance lateral phoria using near point vision and phoria screener 30. The parallel lines of a Maddox rod are held horizontally in front of the right eye. If the vertical red line is seen directly through the small light source produced by lamp 36 (white color), no phoria is present. If the vertical red line is seen at the fourth letter or beyond, to the left of lamp opening 34 or beyond, or the second letter to the right of lamp opening 34 or beyond, the patient is referred.

Binocularity is screened with the Worth 4-Dot Tester 22 by holding red-green glasses with one red lens and one green lens in front of the eyes with the red lens in front of the right eye and the green lens in front of the left eye. If the patient does not report seeing four dots, he is referred.

To operate the electrical system of the present invention, the male plug 28 at the end of power cable 23 is plugged into a conventional grounded 110 volt electrical outlet. Power cable 56 which is connected by a conventional male plug, preferably grounded, at the end thereof is plugged into female receptacle 52 located on lamp base 44. With the entire electrical system energized current flows through step down transformer (110 volt/12 volt) 50 and diodes 55,55 to switch 26. Activation of switch 26 permits current to flow through stepper relay 54 (Schrack RT 600012) through isolation relay 53 through ballast 46 and lamp 20. Activating switch 26 again permits current to flow through stepper relay 54 and lamp 36. Activating switch 26 again permits current to flow through stepper relay 54 and lamp 40. Activating switch 26 again permits current to flow through stepper relay 54 to shut off lamps 20, 36 and 40. Lamp 32 is on at all times when plug 27 is plugged into female plug 28. To provide ease of servicing, electrical components are where possible preferably mounted on printed circuit board 51. All circuits with the exception of that which energizes lamp 20 are low voltage circuits to provide maximum safety for the operator and patient.

From the foregoing it is apparent that the purposes and objects of the invention have been accomplished. While these specific details have been herein shown and described, the invention is not to be confined thereto as changes and alterations may be made without departing from the spirit thereof as defined by the appended claims.

What is claimed is:

1. A portable vision screening kit comprising a carrying case having a removable front panel, said carrying case housing removable eye screening chart means slidably mounted on a pair of tracks for screening for distance visual acuity, means for illuminating said removable eye testing chart shielded from direct view, means for screening for distance phoria having means of illumination capable of providing a small light source, removable hand held means for screening for near phoria and near point vision having means of illumination capable of providing a small light source and means for screening for binocularity having means of illumination capable of providing a small light source and switch means to control the illumination for said means for screening for distance visual acuity, said means for screening for distance and near phoria and said means for screening for binocularity, and means for providing electrical energy to said switch means and means of illumination.

2. A portable vision screening kit as claimed in claim 1 wherein said removable hand held means for screening for near point vision and near phoria comprises a handle element and a chart element with means to conduct electricity passing through said handle element to said source of illumination mounted in said handle element.

3. A portable vision screening kit as claimed in claim 2 wherein said means for providing electrical energy is provided by a step down transformer to supply low voltage electricity to said switch means and to said means of illumination used with said means for screening for distance and near phoria and binocularity.

4. A portable vision screening kit as claimed in claim 2 wherein said removable hand held means for screening for near point phoria and near point vision is detachably connected to said carrying case by coupling means, said means for providing electrical energy is provided with a step down transformer to supply low voltage electricity to said switch means and said means of illumination used with said means for screening for distance and near phoria and binocularity.

5. A portable vision screening kit as claimed in claims 2, 3 or 4 wherein said means of illumination for said distance phoria screening means, said near phoria and near point vision screening means and said binocularity screening means are light emitting diodes.

6. A portable vision screening kit as claimed in claim 1 wherein said means of illumination for said removable eye testing chart is a fluorescent lamp.

7. A portable vision screening kit as claimed in claim 1 wherein said removable front panel is provided with cutouts to permit power and switch cables to pass therethrough and an accessory tray mounted on the inner side thereof.

* * * * *